(12) United States Patent
Sillender

(10) Patent No.: US 10,154,856 B2
(45) Date of Patent: Dec. 18, 2018

(54) THERAPEUTIC SUBSTANCE TRANSFER CATHETER AND METHOD

(71) Applicant: Mark Sillender, Bicton (AU)

(72) Inventor: Mark Sillender, Bicton (AU)

( * ) Notice: Subject to any disclaimer, the term of this patent is extended or adjusted under 35 U.S.C. 154(b) by 186 days.

(21) Appl. No.: 14/760,326

(22) PCT Filed: Feb. 6, 2014

(86) PCT No.: PCT/AU2014/000090
§ 371 (c)(1),
(2) Date: Jul. 10, 2015

(87) PCT Pub. No.: WO2014/121332
PCT Pub. Date: Aug. 14, 2014

(65) Prior Publication Data
US 2015/0359566 A1    Dec. 17, 2015

(30) Foreign Application Priority Data

Feb. 6, 2013    (AU) ................ 2013900397

(51) Int. Cl.
*A61B 17/42*    (2006.01)
*A61F 6/00*    (2006.01)
(Continued)

(52) U.S. Cl.
CPC .............. *A61B 17/42* (2013.01); *A61F 6/00* (2013.01); *A61F 6/18* (2013.01); *A61K 9/0036* (2013.01);
(Continued)

(58) Field of Classification Search
CPC ... A61B 17/42; A61B 2017/4225; A61F 6/18; A61F 6/00; A61K 9/0036; A61M 31/002; A61M 25/1002
See application file for complete search history.

(56) References Cited

U.S. PATENT DOCUMENTS

| 4,976,692 A | 12/1990 | Atad |
|---|---|---|
| 5,150,718 A | 9/1992 | De Nijs |

(Continued)

FOREIGN PATENT DOCUMENTS

| WO | 82/00754 | 3/1982 |
|---|---|---|
| WO | 95/32756 | 12/1995 |

(Continued)

OTHER PUBLICATIONS

Yanushpolsky, et al., "Transcervical placement of a Malecot catheter after hysteroscopic evaluation provides for easier entry into the endometrial cavity for women with histories of difficult intrauterine inseminations and/or embryo transfers: a prospective case series", Fertility and Sterility, vol. 73, No. 2, pp. 402-405, Feb. 2000.

(Continued)

*Primary Examiner* — Amber Stiles
(74) *Attorney, Agent, or Firm* — Hamre, Schumann, Mueller & Larson, P.C.

(57) ABSTRACT

A cervical transfer catheter (10) for transferring a therapeutic substance to an endocervix or other internal mucosal surfaces of a recipient, the catheter (10) comprising: a catheter body (12) having first and second lumens (14) and (16), the second lumen (16) being adapted, in use, to allow passage and retention of a structure containing the therapeutic substance that will be released slowly and continuously. The catheter (10) also comprises an inflatable balloon (20) provided at a distal end of the first lumen (14), the inflatable balloon (20) being designed to be as small as possible in its inflated condition while still being retained in the uterus by virtue of its shape.

22 Claims, 4 Drawing Sheets

(51) Int. Cl.
*A61M 31/00* (2006.01)
*A61K 9/00* (2006.01)
*A61F 6/18* (2006.01)
*A61M 25/10* (2013.01)

(52) U.S. Cl.
CPC ... *A61M 31/002* (2013.01); *A61B 2017/4225* (2013.01); *A61M 25/1002* (2013.01)

(56) References Cited

U.S. PATENT DOCUMENTS

| | | | |
|---|---|---|---|
| 5,383,873 | A | 1/1995 | Hoey et al. |
| 5,451,232 | A | 9/1995 | Rhinehart |
| 5,613,950 | A | 3/1997 | Yoon |
| 6,063,395 | A | 5/2000 | Markkula et al. |
| 6,086,909 | A * | 7/2000 | Harrison ............. A61F 6/08 424/430 |
| 6,476,079 | B1 | 11/2002 | Jukarainen et al. |
| 2002/0082634 | A1* | 6/2002 | Kammerer ........ A61M 25/1002 606/193 |
| 2003/0229373 | A1 | 12/2003 | Lee |
| 2004/0247674 | A1 | 12/2004 | Haapakumpu |
| 2005/0021069 | A1 | 1/2005 | Feuer |
| 2005/0240211 | A1* | 10/2005 | Sporri ............. A61B 17/42 606/193 |
| 2006/0058831 | A1* | 3/2006 | Atad ............. A61M 25/1002 606/193 |
| 2007/0151565 | A1* | 7/2007 | Sanders Acedo ....... A61F 6/144 128/839 |
| 2008/0047563 | A1* | 2/2008 | Tal ............. A61F 6/18 128/831 |
| 2009/0054871 | A1* | 2/2009 | Sharkey ............. A61B 18/04 604/515 |
| 2011/0017219 | A1* | 1/2011 | de Graaff ............. A61F 6/14 128/833 |
| 2015/0342642 | A1 | 12/2015 | Sillender |

FOREIGN PATENT DOCUMENTS

| | | | |
|---|---|---|---|
| WO | 97/16217 | 5/1997 | |
| WO | 2012/013229 | 2/2012 | |
| WO | WO 2012013229 A1 * | 2/2012 | ........... A61K 9/0036 |

OTHER PUBLICATIONS

Supplementary European Search Report issued in European Application, No. 14748819.1, dated Sep. 19, 2016, 5 pages.
Supplementary European Search Report issued in European Application, No. 14748804.3, dated Aug. 16, 2016, 9 pages.
Office Action issued in European Patent Application No. 14748804.3, dated Apr. 26, 2018, 4 pages.

* cited by examiner

THERAPEUTIC SUBSTANCE TRANSFER CATHETER AND METHOD

FIELD OF THE INVENTION

The present invention relates to a new therapeutic substance transfer catheter and relates particularly, though not exclusively, to such a therapeutic substance transfer catheter for use in administering medication in a controlled manner over a sustained time period. The invention also relates to an improved method of transferring a therapeutic substance in a controlled manner over a sustained time period.

BACKGROUND TO THE INVENTION

The most common method of delivering a therapeutic substance, such as a drug or other medication, to the human body is by ingestion. However this method is not suitable for therapeutic substances which may be inactivated by digestive enzymes or by passage through the liver. Ingestion is also less effective for delivering a therapeutic substance in a controlled manner over an extended period of time. Therefore, other routes of administration are used such as a vaginal pessary or rectal suppository. Alternatively, methods of delivering a therapeutic substance in a controlled manner have been developed, including surgical and non-surgical implants.

One of the problems with the vaginal and rectal routes is that the medication often drops out after administration. Also, current implant technology either cannot be removed if it is dissolvable in the skin or elsewhere, or needs to be removed surgically if it is contained within a non-dissolvable structure and then reinserted surgically.

Other examples of known prior art methods of administrating medication are the various intrauterine systems (IUS) and devices (IUD), utilised for the controlled release of a hormone or contraceptive substance. However with this type of system the device needs to be removed and replaced completely if the dose of medication runs out, which is not only inconvenient, but can also be difficult and may be associated with infection. Also, these routes work poorly when it comes to sustained systemic absorption due to their location high in the uterine cavity where the medication tends to linger locally rather than be absorbed into the rest of the body.

The present invention was developed with a view to providing a cervical transfer catheter and method for the controlled release of a therapeutic substance which is less susceptible to the above-noted disadvantages of the prior art. Although the device and method will be described with particular reference to human use, it will be understood that the device and method may also be used with animals.

References to prior art in this specification are provided for illustrative purposes only and are not to be taken as an admission that such prior art is part of the common general knowledge in Australia or elsewhere.

SUMMARY OF THE INVENTION

According to one aspect of the present invention there is provided a cervical transfer catheter for transferring a therapeutic substance to an endocervix or other internal mucosal surfaces of a recipient, the catheter comprising:
a catheter body having first and second lumens, the second lumen being adapted, in use, to allow passage and retention of a removable stent containing the therapeutic substance that will be released slowly and continuously; and, an inflatable balloon provided at a distal end of the first lumen, the inflatable balloon being designed to be as small as possible in its inflated condition whilst still being retained in the recipients uterus by virtue of its shape.

Typically the stent is a flexible stent, although a rigid stent is also possible. Preferably the stent has a solid body and is made of a polymer, or covered by a permeable membrane, that allows for the controlled release of the therapeutic substance. Alternatively the stent comprises a hollow outer body made of a permeable polymer or membrane, which is then filled with a liquid, gel or solid material containing the therapeutic substance. In one embodiment the hollow outer body contains a plurality of segments of a material containing the therapeutic substance, each segment being customisable to the particular needs of the recipient.

Preferably a portion or the whole of the catheter body is also constructed of polymer or contains a permeable membrane that allows the passage of the therapeutic substance from the stent into the endocervix or other internal mucosal surfaces of the recipient.

Because of the rich local blood supply, delivery of a therapeutic substance to the adjacent bladder and urethra, anus and rectum, pelvic floor musculature, pelvic nerves and pelvic blood vessels, and hence the entire body is possible. The therapeutic substance supplied via the catheter may be useful in the full range of medical conditions, which are detailed below. The removable stent containing the therapeutic substance may be easily changed or replaced by simple exchange of the stent. The removable stent containing the therapeutic substance is easily replaceable and customisable to allow for dosage variation or multiple combinations of drugs, for example, by simply using different segments to construct a bespoke structure, or easy replenishment when medications prove to be satisfactory for the patient and have simply run out over time.

Preferably the shape of the balloon is adapted in its inflated state to conform to just the lowest part of the uterus. Preferably the balloon is shaped to conform to the lowest part of the uterus both transversely and in an anterior-posterior direction. Preferably the balloon is shaped in a concave way transversely on its superior aspect, which provides the volume necessary for catheter retention and conforms to the transverse uterine shape.

Typically the balloon comprises first and second arms, which in an inflated state extend upwards transversely within the uterus, at an angle approximating the slope of the inner transverse walls of the flattened uterine cavity.

Another possible variation helps retention of the balloon and hence the catheter. Optionally the balloon may be augmented by inferior protuberances providing extra resistance to expulsion of the catheter. These protuberances typically deflate and become flaccid when the balloon is deflated allowing atraumatic removal. Advantageously these protuberances also enhance the seal of the balloon, when inflated, to the lower part of the uterus, further blocking expulsion of the catheter.

Preferably the portion of the outer catheter body located on the vaginal aspect of the cervix is secured by means of a locking plastic device or an inflatable balloon device for holding the correctly positioned catheter in place more securely preventing displacement of the device. Either one of these devices preferably slide up and down the outer catheter body prior to be being secured or inflated so it lies snugly adjacent to the external aspect of the cervix, securing it in a stable position without movement. This allows for good security, despite variation in the length of the cervix in different women. The length of the catheter is such that it limits that portion of its length protruding into the vagina to enhance comfort. However, it still remains accessible in order to allow inflation of the balloon using the first lumen, or passage of a structure containing the therapeutic substance through the second lumen.

According to another aspect of the present invention there is provided an improved method of transferring a therapeutic substance to an endocervix or other internal mucosal surfaces of a recipient's body, the method comprising the steps of:

providing an outer catheter body having first and second lumens, the first lumen having an inflatable balloon provided at its distal end;

inserting the outer catheter body into the uterus through the cervix;

inflating the balloon with fluid so that the outer catheter body is retained in the uterus and endocervix;

inserting a removable stent containing a therapeutic substance into the second lumen; and, retaining the outer catheter body in the uterus and endocervix for an extended period of time wherein, in use, the therapeutic substance will be released slowly and continuously in a controlled manner into the endocervix or other internal mucosal surfaces and thence into the rest of the recipient's body.

Typically the step of inserting a removable stent containing a therapeutic substance is performed by inserting a removable, preferentially flexible plastic stent, or a removable, hollow plastic stent containing a therapeutic substance in another configuration, that is lockable in position by a locking mechanism. The locking mechanism may be a Luer-Lok (Trademark) or one of several other standard locking systems.

The method may be used to deliver therapeutic substances to pelvic organs or adjacent structures in other medical applications, including the bladder and urethra, anus and rectum, pelvic floor musculature, pelvic nerves and pelvic blood vessels.

Specific potential applications in the field of obstetrics & gynaecology include, but are not limited to:

Therapeutics to reduce urinary stress incontinence of the bladder, urgency symptoms and urge incontinence affecting the bladder, recurrent urinary tract infections, painful bladder syndrome or interstitial cystitis;

Therapeutics to provide treatment of inflammatory bowel disease, for example corticosteroids, 5-aminosalicyclic acid and it's analogues and derivatives;

Antispasmodics to reduce the pain associated with some anal conditions. Examples would be Calcium channel blockers, for instance Dihydropyridine calcium channel blockers, including but not limited to nifedipine, amlodipine, nicardipine, nimodipine etc; Phenylalkylamine calcium channel blockers like verapamil; Benzothiazepine calcium channel blockers like diltiazem; and non-selective agents like mibefradil, bepridil, fluspirilene, and fendiline; nitric oxide, nitroglycerine, isosorbide mononitrate, nitroprusside and other nitric acid donors;

Muscular antispasmodics to reduce vaginismus. Examples are drugs that reduce acetylcholine levels like trihexyphenidyl hydrochloride, benztropine mesylate, diazepine and the other benzodiazepines, levodopa, reserpine, carbamazepine and their derivatives and analogues;

Therapeutics to control neuralgic-related pain. Examples are antidepressant medication such as amitriptyline, imipramine, nortriptyline, duloxetine; and antiseizure medication such as carbamazepine, gabapentin, lamotrigine, phenytoin, pregabalin, sodium valproate;

Therapeutics to enhance female sexual response, for instance sildenafil and other phosphodiesterase type 5 inhibitors, their derivatives and their analogues;

Analgesics for painful pelvic conditions like endometriosis, adenomyosis, inflammatory bowel disease, irritable bowel syndrome, chronic pelvic pain, diverticultis, adhesions, painful bladder syndromes, interstitial cystitis, and infections of any structure within the pelvis;

Oestrogens including oestradiol, oestriol, oestrone and other synthetic oestrogenic derivatives, natural oestrogens including conjugated equine oestrogens, and their derivatives and analogues, to treat vaginal atrophy, dyspareunia, vulval pain and pelvic pain;

Systemic hormone replacement therapy including oestradiol, oestriol, oestrone and other synthetic oestrogenic derivatives, natural oestrogen, conjugated equine oestrogens, progesterone and other synthetic progestin derivatives, androgens including testosterone, dihydrotestosterone, androstenedione and their derivatives and analogues; and, Hormones used to initiate, induce or augment labour, for instance oxytocin and prostaglandin $I_2$, prostaglandin $E_2$ and prostaglandin $F_{2\ alpha}$ and their analogues and derivatives.

A wide variety of other specific applications across the field of medicine may also be applicable.

Throughout the specification, unless the context requires otherwise, the word "comprise" or variations such as "comprises" or "comprising", will be understood to imply the inclusion of a stated integer or group of integers but not the exclusion of any other integer or group of integers. Likewise the word "preferably" or variations such as "preferred", will be understood to imply that a stated integer or group of integers is desirable but not essential to the working of the invention.

BRIEF DESCRIPTION OF THE DRAWINGS

The nature of the invention will be better understood from the following detailed description of several specific embodiments of a therapeutic substance transfer catheter and improved method of transferring a therapeutic substance, given by way of example only, with reference to the accompanying drawings, in which.

DETAILED DESCRIPTION OF PREFERRED EMBODIMENTS

Figure 1:
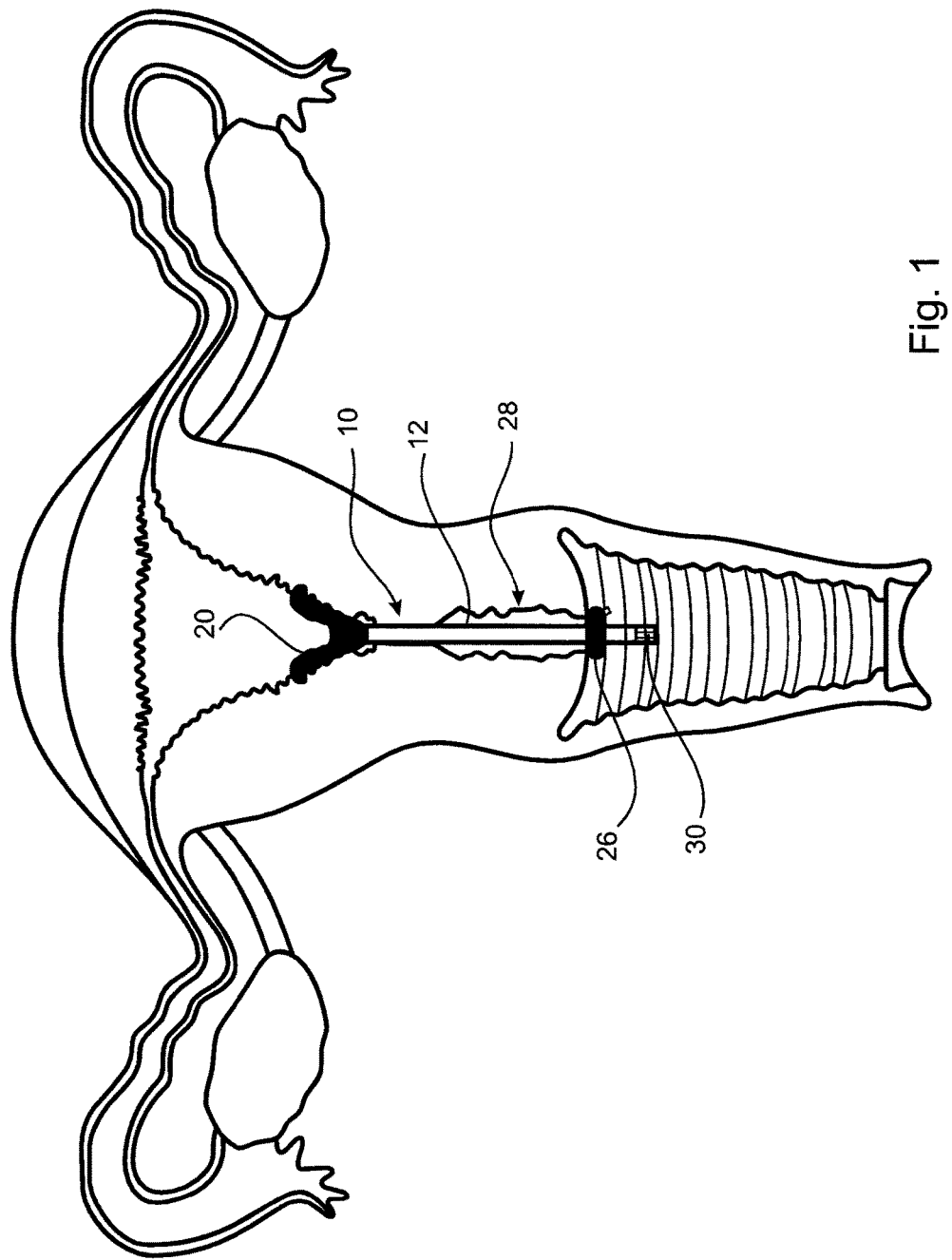
FIG. 1 illustrates a first embodiment of therapeutic substance transfer catheter inserted into a uterus through the cervix of the recipient.
Figure 2:
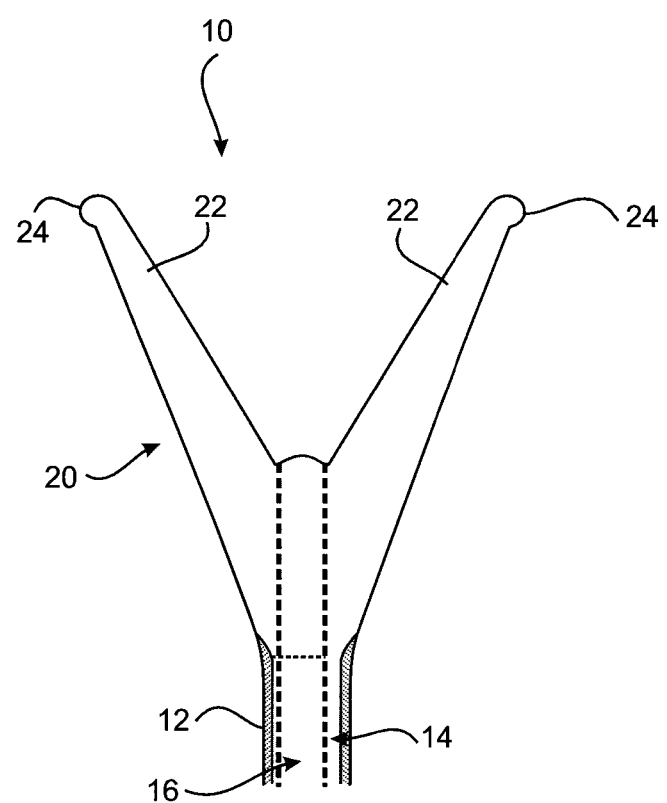
FIG. 2 illustrates the shape of a balloon on the distal end of the cervical transfer catheter of FIG. 1 in its inflated state.
Figure 3:
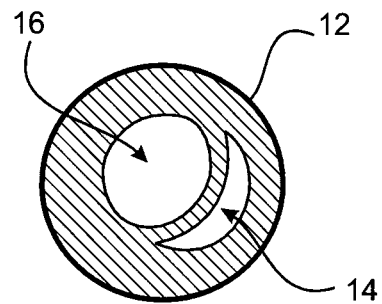
FIG. 3 is a cross-section view of the outer catheter body of the cervical transfer catheter of FIG. 1.

A first embodiment of an cervical transfer catheter 10 in accordance with the invention, as illustrated in FIGS. 1 to 3, comprises a catheter body 12 having first and second lumens 14, 16 (see FIG. 3). The second lumen 16 is adapted, in use, to allow passage and retention of a structure 30 containing the therapeutic substance that will be released slowly and continuously into an endocervix 28 or other internal mucosal surfaces of a recipient. The endocervix is the mucous membrane lining the canal of the cervix uteri and/or the region of the opening of the cervix into the uterine cavity.

An inflatable balloon 20 is provided at a distal end of the first lumen 14. The inflatable balloon 20 is designed to be as small as possible in its inflated condition whilst still being retained in the endocervix 28. In FIG. 3 it can be seen how the cross-sectional shape of the first lumen 14 (for balloon inflation) of the outer catheter body 12 is crescent shaped.

The shape of the balloon 20 is preferably adapted in its inflated state to conform to just the lowest part of the uterus. Preferably the balloon 20 is shaped to conform to the lowest part of the uterus both transversely and in an anterior-posterior direction. Preferably the balloon is shaped in a concave way transversely on its superior aspect, which provides the volume necessary for catheter retention and conforms to the transverse uterine shape, but leaves as much endometrium accessible as possible. Preferably the balloon is convex in an anterior-posterior dimension on its superior aspect, taking up minimal room in the smaller anterior-posterior dimension of the flattened uterine cavity, whilst still being retained.

In the illustrated embodiment the balloon 20 comprises first and second arms 22, which in an inflated state extend upwards transversely within the uterus, at an angle approximating the slope of the inner transverse walls of the flattened uterine cavity.

Another possible variation helps retention of the balloon 20 and hence the catheter: Optionally the balloon 20 may be augmented by inferior protuberances 24 providing extra resistance to expulsion of the catheter body 12. Several protuberances may be provided on each balloon to enhance tactile resistance to expulsion. These protuberances 24 typically deflate and become flaccid when the balloon 20 is deflated allowing atraumatic removal. Advantageously these protuberances 24 also enhance the seal of the balloon 20 to the lower part of the uterus, blocking expulsion.

The use of protuberances on the balloon 20 is not the only way to secure the catheter within the uterus. For example, an assembly of two similarly shaped plastic arms with distal hinges could be deployed. The plastic arms would be straight (continuous with the catheter) upon insertion, but could then be pushed transversely, articulating via their hinges, at a chosen time by using the stent, pressing on a plastic protuberance. Then when removal occurs, the stent can be pulled out, allowing the plastic arms to fold back vertically facilitating catheter extraction.

Preferably the portion of the catheter body 12 on the vaginal aspect of the cervix is secured by means of a plastic locking device or an inflatable locking balloon device 26 for holding the correctly positioned catheter in place more securely following embryo transfer. Either one of these devices preferably slides up and down the catheter body 12 prior to be being secured or inflated, so that it lies snugly adjacent to the external aspect of the cervix 18, securing it in a stable position without movement, as shown in FIG. 1. This allows for secure retention of the catheter 10, despite variation in the length of the cervix in different women. The portion of the outer catheter body 12 on the vaginal aspect of the cervix can also be secured by simply via increased friction and a snug fit.

Figure 5:
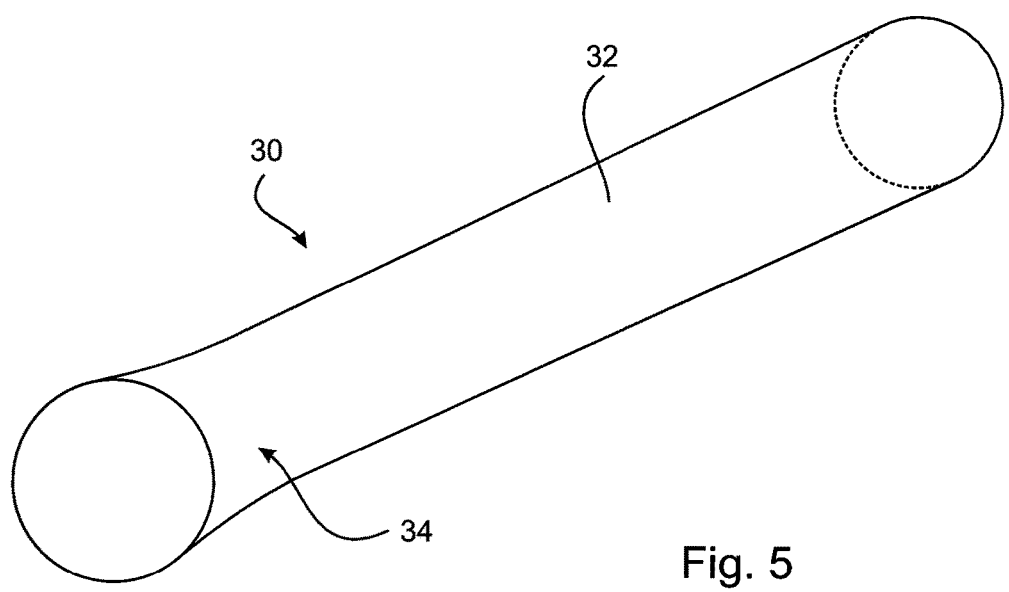
FIG. 5 is a side view of a structure containing a therapeutic substance employed in the cervical transfer catheter of FIG. 1; and, FIG. 6 illustrates an alternative design for the structure containing a therapeutic substance employed in the cervical transfer catheter.

Preferably the structure containing the therapeutic substance is a removable, flexible stent 30 although the stent may also be rigid. FIG. 5 illustrates a stent 30 having a solid body 32. Preferably the body 32 of the stent is made of a polymer, or covered by a permeable membrane, that allows for the controlled release of the therapeutic substance. Alternatively, the stent 30 may comprise a hollow outer body made of a permeable polymer or membrane, which is then filled with a liquid, gel or solid material containing the therapeutic substance.

The stent 30 may be secured in the catheter body 12 by a locking mechanism, typically a Luer-Lok (Trademark), a slot-type lock or a similar securing device. As can be seen most clearly in FIG. 5, one end of the stent body 32 preferably has a tapered neck 34 to secure the stent 30 in the second lumen 16 of the catheter by a frictional fit. The top of the stent 30 would typically be gently convex to match the adjacent parts of the balloon 20.

Figure 6:
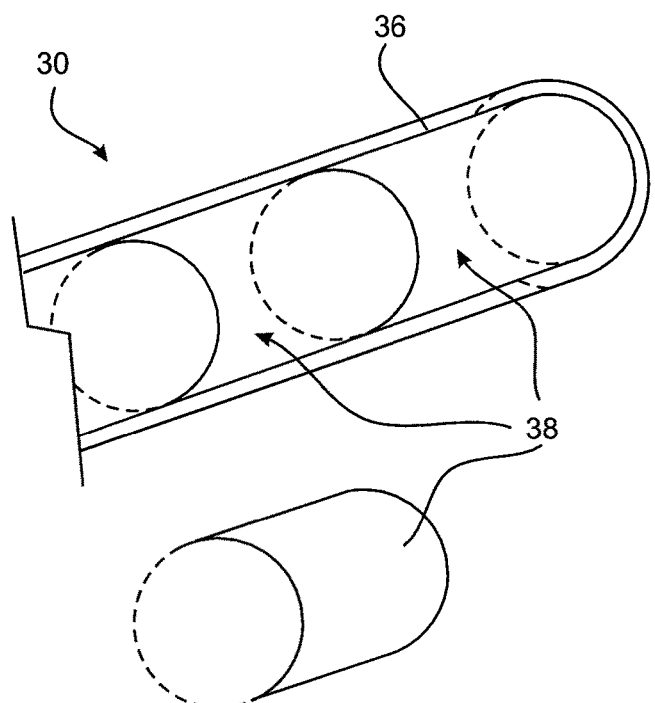

FIG. 6 illustrates an alternative configuration for the stent 30. This embodiment utilises a hollow outer body 36 made of a permeable polymer or membrane, which is then filled with a plurality of removable segments 38 of material containing the therapeutic substance. Each segment 38 can be filled with a different therapeutic substance and/or configured with a different dosage or rate of substance-release customised to the needs of the recipient. Using different segments 38 allows the device 10 to be fully customised.

Advantageously a portion or the whole of the catheter body 12 is also constructed of a polymer, or contains a permeable membrane, that allows the passage of the therapeutic substance from the stent 30 into the endocervix 28 or other internal mucosal surfaces of the recipient.

Preferably the lumen 16 is blind-ending/closed off at the uterine end, as nothing needs to pass through it into the uterine cavity. When the stent 30 is placed within the lumen 16 it transmits a therapeutic substance through the wall of the catheter body 12. Alternatively the stent 30 occupies the whole lumen 16 and naturally closes off the other end of the lumen, or a lid is provided to close off the lumen.

Figure 4:
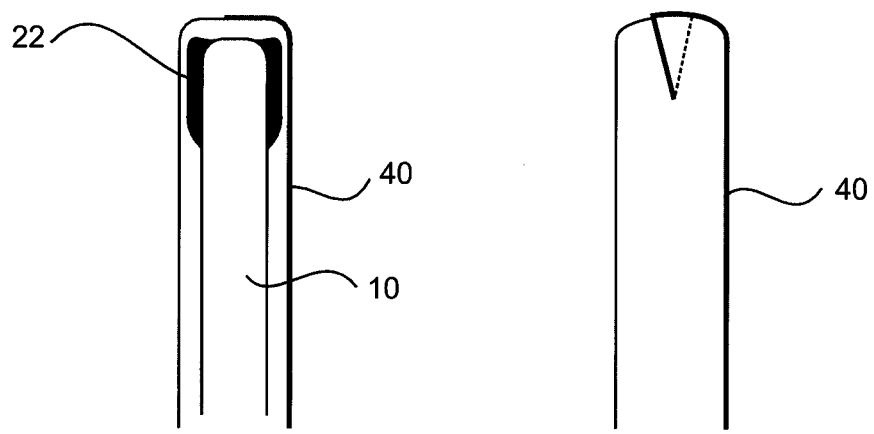
FIG. 4 illustrates a sleeve for insertion of the cervical transfer catheter of FIG. 1.

Advantageously the cervical transfer catheter 10 may be inserted through the cervix and into the uterine cavity within a tight-fitting covering or sleeve 40 (made of silicone or PVC or other flexible material), illustrated in FIG. 4. The sleeve 40 has a split at the top with overlapping portions. Once the catheter 10 has been inserted into the uterus, this silicone sleeve 40 is removed by simply pulling it distally, the split at the top allowing its removal leaving the catheter 10 in place. The sleeve 40 protects the catheter 10 from contacting any potentially infected cervical mucus or infection. The sleeve 40 may be slightly textured or absorbent. This texture or absorbency encourages adherence of any cervical mucus brought into the uterus during the insertion, and thus allows the removal of this mucus when the sleeve 40 is removed.

A preferred method of transferring therapeutic substance into the endocervix 28 or other internal mucosal surfaces of a recipient will now be described with reference to FIG. 1. The method firstly comprises the step of providing an outer catheter body 12 having first and second lumens 14, 16, the first lumen having an inflatable balloon 20 provided at its distal end, as described above. The outer catheter body 12 may be inserted into the uterus through the cervix 18 at the same time or several hours or several days or longer before the delivery of a therapeutic substance is commenced. Then the balloon 20 is inflated with fluid (liquid or gas) so that the outer catheter body 12 is retained in the uterus and cervix 18.

The removable, preferably flexible plastic stent 30 is then placed in the second lumen 16 when controlled release of the therapeutic substance is to commence. The stent 30 containing the therapeutic substance may be easily changed or replaced by simple exchange of the stent. An easily replaceable, customisable stent 30 allows for dosage variation, multiple combinations of drugs by simply using different segments, or easy replenishment when medications are satisfactory for the patient and/or have simply run out over time.

The catheter and method can be used to deliver therapeutic substances not only to the endocervix, but also beyond to adjacent pelvic organs or structures including the rest of the body in other medical applications, particularly in women who have stopped menstruating. Because of the rich local blood supply, delivery of therapeutic substances to the adjacent bladder and urethra, anus and rectum, pelvic floor musculature, pelvic nerves and pelvic blood vessels, and hence the entire body is possible.

Specific potential applications in the field of obstetrics & gynaecology would include, but are not limited to:

Therapeutics to reduce urinary stress incontinence of the bladder, urgency symptoms and urge incontinence affecting the bladder, recurrent urinary tract infections, painful bladder syndrome or interstitial cystitis;

Therapeutics to provide treatment of inflammatory bowel disease, for example corticosteroids, 5-aminosalicyclic acid and it's analogues and derivatives;

Antispasmodics to reduce the pain associated with some anal conditions. Examples would be Calcium channel blockers, for instance Dihydropyridine calcium channel blockers, including but not limited to nifedipine, amlodipine, nicardipine, nimodipine etc; Phenylalkylamine calcium channel blockers like verapamil; Benzothiazepine calcium channel blockers like diltiazem; and non-selective agents like mibefradil, bepridil, fluspirilene, and fendiline; nitric oxide, nitroglycerine, isosorbide mononitrate, nitroprusside and other nitric acid donors;

Muscular antispasmodics to reduce vaginismus. Examples are drugs that reduce acetylcholine levels like trihexyphenidyl hydrochloride, benztropine mesylate, diazepine and the other benzodiazepines, levodopa, reserpine, carbamazepine and their derivatives and analogues;

Therapeutics to control neuralgic-related pain. Examples are antidepressant medication such as amitriptyline, imipramine, nortriptyline, duloxetine; and antiseizure medication such as carbamazepine, gabapentin, lamotrigine, phenytoin, pregabalin, sodium valproate;

Therapeutics to enhance female sexual response, for instance sildenafil and other phosphodiesterase type 5 inhibitors, their derivatives and their analogues;

Analgesics for painful pelvic conditions like endometriosis, adenomyosis, inflammatory bowel disease, irritable bowel syndrome, chronic pelvic pain, diverticulitis, adhesions, painful bladder syndromes, interstitial cystitis, and infections of any structure within the pelvis;

Oestrogens including oestradiol, oestriol, oestrone and other synthetic oestrogenic derivatives, natural oestrogens including conjugated equine oestrogens, and their derivatives and analogues, to treat vaginal atrophy, dyspareunia, vulval pain and pelvic pain;

Systemic hormone replacement therapy including oestradiol, oestriol, oestrone and other synthetic oestrogenic derivatives, natural oestrogen, conjugated equine oestrogens, progesterone and other synthetic progestin derivatives, androgens including testosterone, dihydrotestosterone, androstenedione and their derivatives and analogues; and, Hormones used to initiate, induce or augment labour, for instance oxytocin and prostaglandin $I_2$, prostaglandin $E_2$ and prostaglandin $F_{2\,alpha}$ and their analogues and derivatives.

Specific applications across the field of medicine include the following.

Gastrointestinal medications that can be utilised are as follows. Antispasmodics including antimuscarinics (atropine sulphate, dicycloverine hydrochloride, propantheline bromide, hyoscine butylbromide), alverine citrate, mebeverine hydrochloride. Motility stimulants including metoclopramide, domperidone. Anti-secretory drugs including cimetidine, famotidine, nizatidine, ranitidine. Proton pump inhibitors including esomeprazole, lansoprazole, omeprazole, pantoprazole, rabeprazole. Antimotility drugs including co-phenotrope, loperamide hydrochloride. Anti-inflammatory bowel disease medications including balsalazide sodium, mesalazine, olsalazine sodium, sulfasalazine. Corticosteroids including beclometasone dipropionate, budesonide, hydrocortisone, prednisolone. Immune reposnse modifiers including azathioprine, ciclosporin, mercaptopurine, methotrexate. Laxatives including methylnaltrexone bromide, prucalopride. Glyceryl trinitrate for anal fissures. Ursodeoxycholic acid for prevention of gallstones.

Medications used in the field of cardiology that can be utilised are as follows. Cardiac inotropes including digoxin, enoximone, and milrinone. Diuretics including thiazides (bendroflumethiazide, chlortalidone, cyclopenthiazide, indapamide, metolazone, xipamide), loops (bumetanide, furosemide, torasemide), potassium sparing agents (amiloride hydrochloride, triamterene), and aldosterone antagonists (spironolactone, eplerenone). Anti-arrhythmic drugs including dronedarone, digoxin, verapamil, amiodarone hydrochoride, disopyramide, flecainide acetate, procainamide, propafenone hydrocholride, and beta-blockers (propranolol hydrochloride, acebutolol, atenolol, bisoprolol fumarate, carvedilol, celiprolol hydrochloride, esmolol hydrochloride, labetolol hydrochloride, metoprolol tartrate, nadolol, nebivolol, oxprenolol hydrochloride, pindolol, sotalol hydrochloride, timolol maleate), ivabradine, ranolazine Other medications are anti-hypertensive drugs including hydralazine hydrochloride, prazosin, doxazosin, indoramin, terazosin, sildenafil, methyldopa, clonidine hydrochloride, and moxonidine. Drugs used in heart failure or hypertension including captopril, cilazapril, enalapril maleate, fosinopril sodium, imidapril hydrochloride, lisinopril, moexipril hydrochloride, perindopril erbumine, perindopril arginine, quinapril, rampiril, trandolapril, candesartan cilexetil, eprosartan, irbesartan, losartan potassium, olmesartan medoxomil, telmisartan, valsartan, and aliskiren. Vasodilators include glyceryl trinitrate, isosorbide dinitrate, isosorbide mononitrate, amlodipine, diltiazem hydrochloride, felodipine, isradipine, lacidipine, lercanidipine hydrochloride, nicardipine hydrochloride, nifedipine, nimodipine, verapamil hydrochloride, nicorandil, cilostazol, inositol nicotinate, moxisylyte, naftidrofuryl oxalate, and pentoxifylline Further medications include anticoagulants such as heparin, dalteparin sodium, enoxaparin sodium, tinzaparin sodium, danaparoid sodium, bivalirudin, lepirudin, fondaparinux sodium, warfarin sodium, acenocoumarol, phenindione, dabigatran etexilate, apixaban, and rivaroxaban. Also, antiplatelet drugs including aspirin, clopidogrel, dipyridamole, prasugrel, and ticagrelor. Also, lipid regulating drugs inc atorvastatin, fluvastatin, pravastatin sodium, rosuvastatin, simvastatin, ezetimibe, bezafibrate, ciprofibrate, fenofibrate, gemfibrozil, acipimox, and nicotinic acid Respiratory medications that may be used are as follows: drugs affecting the airways including bambuterol hydrochloride, formoterol fumarate, indacaterol, salbutamol, salmeterol, terbutaline sulphate, ephedrine hydrochloride, ipratropium bromide, tiotropium, theophylline, aminophylline, beclomethasone dipropionate, budesonide, ciclesonide, fluticasone propionate, mometasone furoate, sodium cromoglicate, nedocromil sodium, montelukast, and zafirlukast, roflumilast. Antihistamines including acrivastine, bilastine, cetirizine hydrochloride, desloratadine, fexofenadine hydrochloride, levocetirizine hydrochloride, loratadine, mizolastine, rupatadine, alimemazine tartrate, chlorphenamine maleate, clemastine, cyproheptadine hydrochloride, hydroxyzine hydrochloride, ketotifen, and promethazine hydrochloride.

Drugs having a central nervous system effect are as follows. Anti-anxiety medication including nitrazepam, flurazepam, loprazolam, lormetazepam, temazepam, zaleplon, zolpidem tartrate, zopiclone, chloral hydrate, clomethiazole, sodium oxybate, diazepam, alprazolam, chlordiazepoxide hydrochloride, lorazepam, and oxazepam. Anti-psychotic medication including benperidol, chlorpromazine hydrochloride, flupentixol, haloperidol, levomepromazine, pericyazine, perphenazine, pimozide, prochlorperazine, promazine hydrochloride, sulpiride, trifluoperazine, zuclopenthixol, zuclopenthixol actetate, amisulpride, aripiprazole, clozapine, olanzapine, paliperidone, quetiapine, risperidone, flupentixol decanoate, fluphenazine decanoate, olanzapine embonate, pipotiazine palmitate, and zuclopenthixol decanoate.

Further medications include antimanic drugs including asenapine, carbamazepine, valproic acid, lithium carbonate, and lithium citrate. Antidepressant drugs including amitriptyline hydrochloride, clomipramine hydrochloride, dosulepin hydrochloride, doxepin, imipramine hydrochloride, lofepramine, nortriptyline, trimipramine, mianserin hydrochloride, trazodone hydrochloride, phenelzine, isocarboxazid, tranylcypromine, moclobemide, citalopram, escitalopram, fluoxetine, fluvoxamine maleate, paroxetine, sertraline, agomelatine, duloxetine, mirtazapine, reboxetine, tryptophan, venlafaxine. Antinausea medication includes cinnarizine, cyclizine, promethazine hydrochloride, promethazine teoclate, droperidol, domperidone, metoclopramide hydrochloride, granisetron, ondansetron, palonosetron, aprepitant, fosaprepitant, nabilone, hyoscine hydrobromide, and betahistine dihydrochloride.

Analgesic medication includes aspirin, paracetamol, nefopam hydrochloride, buprenorphine, codeine phosphate, diamorphine hydrochloride, dihydrocodeine tartrate, dipipanone hydrochloride, fentanyl, hydromorphone hydrochloride, meptazinol, methadone hydrochloride, morphine salts, oxycodone hydrochloride, papaveretum, pentazocine, pethidine hydrochloride, tapentadol, and tramadol hydrochloride. Antimigraine medication includes pizotifen, and clonidine hydrochloride.

Antiepileptic medication includes carbamazepine, eslicarbazepine acetate, oxcarbazepine, ethosuximide, gabapentin, pregabalin, lacosamide, lamotrigine, levetiracetam, phenobarbital, pimidone, phenytoin, retigabine, rufinamide, tiagabine, topiramate, sodium valproate, vigabactrin, zonisamide, clobazam, and clonazepam. Antiparkinsonian medication includes apomorphine hydrochloride, bromocriptine, cabergoline, pergolide, pramipexole, ropinirole, rotigotine, levodopa, co-beneldopa, co-careldopa, rasagiline, selegiline hydrochloride, entacapone, tolcapone, amantadine hydrochloride, orphenadrine hydrochloride, procyclidine hydrochloride, and trihexyphenidyl hydrochloride Drugs used in the treatment of substance dependence include acamprosate calcium, disulfiriam, naltrexone, bupropion hydrochloride, nicotine, varenicline, buprenorphine, methadone hydrochloride, and naltrexone hydrochloride. Dementia medication includes donepezil, galantamine, memantine hydrochloride, and rivastigmine.

Medications used in the management of endocrine conditions include the following. Insulins especially intermediate-acting and long-acting preparations. Antidiabetic drugs including glibenclamide, gliclazide, glimepiride, glipizide, tolbutamide, metformin, acarbose, exenatide, linagliptin, liraglutide, nateglinide, pioglitazone, repaglinide, saxagliptin, sitagliptin, and vildagliptin. Thyroxines including levothyroxine sodium, liothyronine sodium, and armour thyroid. Antithyroid drugs include carbimazole and propylthiouracil. Steroids including fludrocortisone acetate, betamethasone, deflazacort, dexamethasone, hydrocortisone, methylprednisolone, prednisolone, prednisone, and triamcinolone.

Female sex hormones may be utilised including oestrogens (conjugated equine oestrogens, oestradiol, oestradiol valerate, ethinyloestradiol, oestriol, mestranol and their analogues and derivatives), tibolone, raloxifene hydrochloride, progestogens (progesterone, dydrogesterone, medroxyprogesterone acetate, megestrol acetate, levonorgestrel, dienogest, norethisterone, norethisterone acetate, norgestrel, desogestrel, norgestimate, gestodene, drospirenone, etynodiol diacetate and their analogues and derivatives), and testosterone esters (enantate, propionate, deconoate, undecanoate, phenylpropionate, isocaproate), dehydroepiandrosterone and mesterolone. Also selective progestogen-receptor modulators inc ulipristal acetate and other members of the same family. Also chorionic gonadotrophin, choriogonadotropin alfa, corifollitropin alfa, follitropin alfa and beta, human menopausal gonadotrophins, lutropin alfa, gonadorelin, Other hormones that can be utilised include somatropin, human growth hormone, desmopressin, vasopressin, tolvaptan. Hormone antagonists include anastrozole, exemestane, fulvestrant, letrozole, tamoxifen, and toremifene. Drugs affecting bone metabolism including calcitonin, parathyroid hormone, teriparatide, bisphosphonates (alendronic acid, disodium etidronate, disodium pamidronate, ibandronic acid, risedronate sodium, sodium condronate, zoledronic acid, denosumab, and strontium ranelate. Other endocrine drugs include bromocriptine, cabergoline, quinagolide, cetrorelix, danazol, ganirelix, buserelin, goserelin, histrelin, leuprorelin acetate, nafarelin, and triptorelin.

Medications used for treating infections may be utilised. These include the following antibiotics. Penicillins (benzylpenicillin sodium, phenoxymethylpenicillin, flucoxacillin, temocillin, amoxicillin, ampicillin, co-amoxiclav, co-fluampicil, piperacillin, tazobactam, ticarcillin with clavulanic acid, and pivmecillinam hydrochloride. Cephalosporins, carbapenems and other beta-lactams (cefaclor, cefadroxil, cephalexin, cefixime, cefotaxime, cefpodoxime, cefradine, ceftazidime, ceftriaxone, cefuroxime, doripenem, ertapenem, imipenem with cilastatin, meropenem, and aztreonam). Tetracycline, demecolcycline hydrochloride, doxycycline, lymecycline, minocycline, oxytetracycline, and tigecycline. Aminoglycosides (gentamicin, amikacin, tobramycin). Macrolides (azithromycin, clarithromycin, erythromycin, and telithromycin). Other antibiotics include clindamycin, chloramphenicol, sodium fusidate, vancomycin, teicoplanin, daptomycin, linezolid, colistimethate sodium, co-trimoxazole, sulfadiazine, trimethoprim, metronidazole, tinidazole, ciprofloxacin, levofloxacin, moxifloxacin, nalidixic acid, norfloxacin, ofloxacin, nitrofurantoin, and methenamine hippurate Other infections can be treated. Antifungals include fluconazole and itraconazole. Antivirals include abacavir, didanosine, emtricitabine, lamivudine, tenofovir disoproxil, zidovudine, atazanavir, darunavir, fosamprenavir, indinavir, lopinavir, ritonavir, nelfinavir, saquinavir, tipranavir, efavirenz, etravirine, nevirapine, enfuvirtide, maraviroc, raltegravir, acyclovir, famciclovir, inosine pranobex, valaciclovir, adefovir dipivoxil, entecavir, telbivudine, boceprevir, and telaprevir. Antimalarials include artemether with lumefantrine, chloroquine, mefloquine, primaquine, proguanil hydrochloride, atovaquone, pyrimethamine, sulfadoxine, and quinine. Anti TB drugs include capreomycin, cycloserine, ethambutol hydrochloride, isoniazid, pyrazinamide, rifabutin, rifampicin, and streptomycin.

Medications which may be used in obstetrics and gynaecology include carbetocin, carboprost, dinoprostone, ergometrine maleate, gemeprost, oxytocin, mifepristone, atosiban, salbutamol, and terbutaline. Antifungals including clotrimazole, miconazole, econazole, fenticonazole may be used. Drugs used for restoring the vaginal environment including clindamycin, metronidazole, and lactic acid may be used. Contraceptives including combined contraception and progestogen-only contraception may be used using combinations and/or varying amounts of the female sex hormones noted above. Similarly hormone replacement therapy may also use varying combinations of the female sex hormones listed above.

Drugs for urinary dysfunction may be used including darifenacin, duloxetine, fesoterodine fumarate, flavoxate hydrochloride, oxybutynin hydrochloride, propantheline bromide, propiverine hydrochloride, solifenacin succinate, tolterodine tartrate, trospium chloride, alfuzosin hydrochloride, doxazosin, indoramin, prazosin, tamsulosin hydrochloride, terazosin, bethanechol chloride, and distigmine bromide. Drugs used to aid sexual response include sildenafil, tadalafil, and vardenafil. Other medications include interferon alfa, peginterferon alfa, interferon beta, interferon gamma-1b, and immunosuppressants such as ciclosporin, tacrolimus, and sirolimus.

Drugs may be utilised that are used in musculoskeletal & joint disease. These include ibuprofen, naproxen, fenoprofen, flurbiprofen, dexketoprofen, ketoprofen, tiaprofenic acid, diclofenac sodium, diclofenac potassium, aceclofenac, etodolac, acemetacin, indomethacin, mefanamic acid, meloxicam, nabumetone, piroxicam, sulindac, tenoxicam, tolfenamic acid, ketorolac, parecoxib, etoricoxib, celecoxib, and other NSAIDs & Cox-2 inhibitors. Also aspirin. Also, sodium aurothiomalate, penicillamine, chloroquine, hydroxychloroquine sulphate, allopurinol, febuxostat, probenecid, sulfinpyrazone, glucosamine, baclofen, cannabis extract, dantrolene sodium, diazepam, tizanidine, and quinine may all be utilised.

Complimentary medications may also potentially be utilised via the device. Herbal supplements, of which there are many, can be utilised if they are thought to give medical benefit when applied by this route.

Now that preferred embodiments of the therapeutic substance transfer catheter and method of transfer of a therapeutic substance have been described in detail, it will be apparent that the described embodiments provide a number of advantages over the prior art, including the following:

(i) The therapeutic substance is delivered directly to an internal mucosal surface and absorbed without inactivation by digestive enzymes or by passage through the liver.
(ii) The therapeutic substance does not drop out after administration (unlike a vaginal pessary or rectal suppository).
(iii) The method provides a for a sustained mode of action without peaks or troughs over an extended period, thus allowing lower doses and preventing problems of compliance with medication—this is vital for many medications.
(iv) Another advantage of the catheter and method is that it allows customisation and relatively easy changes of medication unlike current implant technology, which needs to be removed surgically (if it can be removed at all); and unlike the current intra-uterine system, which needs to be removed entirely and replaced completely if the dose of medication runs out, which lacks convenience, can be difficult and may be associated with infection.

It will be readily apparent to persons skilled in the relevant arts that various modifications and improvements may be made to the foregoing embodiments, in addition to those already described, without departing from the basic inventive concepts of the present invention. For example, the shape of the balloon at the distal end of the outer catheter body may vary significantly from that shown in the illustrated embodiments. The balloon may be of any suitable shape that will still retain the catheter in the uterus. The stent may be of any suitable configuration, and also be compromised of a hollow tube filled with a solid, liquid or gel. Therefore, it will be appreciated that the scope of the invention is not limited to the specific embodiments described.

The invention claimed is:

1. A cervical transfer catheter for transferring a therapeutic substance to an endocervix or other internal mucosal surfaces of a recipient, the catheter comprising:
    a removable stent containing the therapeutic substance;
    a catheter body having first and second lumens, the second lumen being adapted, in use, to allow passage and retention of the removable stent, wherein the second lumen is designed to retain the removable stent after the catheter body has been inserted in a recipient's uterus in order to release the therapeutic substance to the endocervix or other internal mucosal surfaces of the recipient; and,
    an inflatable balloon provided at a distal end of the first lumen, the inflatable balloon being designed to be as small as possible in its inflated condition whilst still being retained in the uterus and endocervix by virtue of its shape so as to retain a portion of the catheter body within the recipient's uterus for a minimum period of several hours,
    wherein the balloon has a first surface that in use contacts a uterine surface of the recipient, and a second, non-contact surface opposite the first surface, and the second, non-contact surface has a generally concave shape,
    and wherein the balloon comprises first and second arms, which in the inflated condition extend upwards transversely within the recipient's uterus.

2. A cervical transfer catheter for transferring a therapeutic substance as defined in claim 1, wherein the stent is a flexible stent.

3. A cervical transfer catheter for transferring a therapeutic substance as defined in claim 2, wherein the stent comprises a hollow outer body made of a permeable polymer or membrane, which is then filled with a liquid, gel or solid material containing the therapeutic sub stance.

4. A cervical transfer catheter for transferring a therapeutic substance as defined in claim 3, wherein the hollow outer body contains a plurality of segments of a material containing the therapeutic substance, each segment being customisable to the particular needs of the recipient.

5. A cervical transfer catheter for transferring a therapeutic substance as defined in claim 2, wherein a portion or the whole of the catheter body is also constructed of a polymer or contains a permeable membrane that allows the passage of the therapeutic substance from the stent into the endocervix or other internal mucosal surfaces of the recipient.

6. A cervical transfer catheter for transferring a therapeutic substance as defined in claim 2, wherein the removable stent containing the therapeutic substance is changed or replaced by exchange of the removable stent.

7. A cervical transfer catheter for transferring a therapeutic substance as defined in claim 4, wherein the removable stent containing the therapeutic substance is replaceable and customisable to allow for dosage variation or multiple combinations of drugs, by using different segments to construct a bespoke structure, or replenishment when medications prove to be satisfactory for the patient and have run out over time.

8. A cervical transfer catheter for transferring a therapeutic substance as defined in claim 1, wherein the stent has a solid body.

9. A cervical transfer catheter for transferring a therapeutic substance as defined in claim 8, wherein the stent is made of a polymer, or covered by a permeable membrane, that allows for the controlled release of the therapeutic substance.

10. A cervical transfer catheter for transferring a therapeutic substance as defined in claim 1, wherein the shape of the balloon is adapted in its inflated condition to conform to just a lowest part of the recipient's uterus.

11. A cervical transfer catheter for transferring a therapeutic substance as defined in claim 10, wherein the balloon is shaped to conform to the lowest part of the uterus both transversely and in an anterior-posterior direction.

12. A cervical transfer catheter for transferring a therapeutic substance as defined in claim 1, wherein the balloon is augmented by inferior protuberances providing extra resistance to expulsion of the catheter.

13. A cervical transfer catheter for transferring a therapeutic substance as defined in claim 12, wherein the protuberances deflate and become flaccid when the balloon is deflated allowing atraumatic removal.

14. A cervical transfer catheter for transferring a therapeutic substance as defined in claim 12, wherein the protuberances enhance a seal of the balloon, when in the inflated condition, to a lower part of the uterus, further blocking expulsion of the catheter.

15. A cervical transfer catheter for transferring a therapeutic substance as defined in claim 1, wherein a portion of the catheter body located on a vaginal aspect of the cervix is secured by a locking plastic device or an inflatable balloon device that holds the catheter in place and preventing displacement of the catheter.

16. A cervical transfer catheter for transferring a therapeutic substance as defined in claim 15, wherein the locking plastic device or the inflatable balloon device slides up and down the catheter body prior to being secured or inflated so the locking plastic device or the inflatable balloon device lies snugly adjacent to an external aspect of the cervix.

17. A cervical transfer catheter for transferring a therapeutic substance as defined in claim 1, wherein the length of the catheter is such that it limits that portion of its length protruding into a vagina to enhance comfort but still remains accessible in order to allow inflation of the balloon using the first lumen, or passage of a structure containing the therapeutic substance through the second lumen.

18. An improved method of transferring a therapeutic substance to an endocervix or other internal mucosal surfaces of a recipient, the method comprising:
providing a catheter body having first and second lumens, the first lumen having an inflatable balloon provided at a distal end of the first lumen;
inserting the catheter body into the uterus through the cervix;
inflating the balloon with fluid so that the catheter body is retained in the uterus and endocervix;
inserting a removable, plastic stent, or inserting a removable, hollow plastic stent containing the therapeutic substance into the second lumen, the stent being lockable in position by a locking mechanism; and,
retaining the catheter body in the uterus and endocervix for an extended period of time with the removable stent remaining in the second lumen of the catheter body wherein, in use, the therapeutic substance is released in a controlled manner into the endocervix or other internal mucosal surfaces and thence into the rest of the recipient's body.

19. An improved method of transferring a therapeutic substance as defined in claim 18, wherein the method is used to deliver therapeutic substances to pelvic organs or adjacent structures in other medical applications, including the bladder and urethra, anus and rectum, pelvic floor musculature, pelvic nerves and pelvic blood vessels.

20. An improved method of transferring a therapeutic substance as defined in claim 18, wherein the method is used to deliver therapeutic substances in potential specific applications in the field of obstetrics & gynaecology selected from the group selected from the following:
therapeutics to reduce urinary stress incontinence of the bladder, urgency symptoms and urge incontinence affecting the bladder, recurrent urinary tract infections, painful bladder syndrome or interstitial cystitis;
therapeutics to provide treatment of inflammatory bowel disease, including corticosteroids, 5-aminosalicyclic acid and it's analogues and derivatives; antispasmodics to reduce the pain associated with some anal conditions, including calcium channel blockers, Dihydropyridine calcium channel blockers, including but not limited to nifedipine, amlodipine, nicardipine, nimodipine; Phenylalkylamine calcium channel blockers including verapamil; Benzothiazepine calcium channel blockers including diltiazem; and non-selective agents including mibefradil, bepridil, fluspirilene, and fendiline; nitric oxide, nitroglycerine, isosorbide mononitrate, nitroprusside and other nitric acid donors;
muscular antispasmodics to reduce vaginismus, including drugs that reduce acetylcholine levels comprising trihexyphenidyl hydrochloride, benztropine mesylate, diazepine and the other benzodiazepines, levodopa, reserpine, carbamazepine and their derivatives and analogues;
therapeutics to control neuralgic-related pain, including antidepressant medication comprising amitriptyline, imipramine, nortriptyline, duloxetine; and antiseizure medication comprising carbamazepine, gabapentin, lamotrigine, phenytoin, pregabalin, sodium valproate;
therapeutics to enhance female sexual response, including sildenafil and other phosphodiesterase type 5 inhibitors, their derivatives and their analogues;
analgesics for painful pelvic conditions, including endometriosis, adenomyosis, inflammatory bowel disease, irritable bowel syndrome, chronic pelvic pain, diverticultis, adhesions, painful bladder syndromes, interstitial cystitis, and infections of any structure within the pelvis;

oestrogens including oestradiol, oestriol, oestrone and other synthetic oestrogenic derivatives, natural oestrogens including conjugated equine oestrogens, and their derivatives and analogues, to treat vaginal atrophy, dyspareunia, vulval pain and pelvic pain;

systemic hormone replacement therapy including oestradiol, oestriol, oestrone and other synthetic oestrogenic derivatives, natural oestrogen, conjugated equine oestrogens, progesterone and other synthetic progestin derivatives, androgens including testosterone, dihydrotestosterone, androstenedione and their derivatives and analogues; and, hormones used to initiate, induce or augment labour, including oxytocin and prostaglandin $I_2$, prostaglandin $E_2$ and prostaglandin $F_{2\ alpha}$ and their analogues and derivatives.

21. An improved method of transferring a therapeutic substance as defined in claim 18, wherein the method is used to deliver therapeutic substances in other potential specific applications across the field of medicine selected from the group selected from the following:

gastrointestinal medications: antispasmodics including antimuscarinics (atropine sulphate, dicycloverine hydrochloride, propantheline bromide, hyoscine butylbromide), alverine citrate, mebeverine hydrochloride; motility stimulants including metoclopramide, domperidone, anti-secretory drugs including cimetidine, famotidine, nizatidine, ranitidine; proton pump inhibitors including esomeprazole, lansoprazole, omeprazole, pantoprazole, rabeprazole; antimotility drugs including co-phenotrope, loperamide hydrochloride; anti-inflammatory bowel disease medications including balsalazide sodium, mesalazine, olsalazine sodium, sulfasalazine; corticosteroids including beclometasone dipropionate, budesonide, hydrocortisone, prednisolone; immune response modifiers including azathioprine, ciclosporin, mercaptopurine, methotrexate, laxatives including methylnaltrexone bromide, prucalopride; glyceryl trinitrate for anal fissures, Ursodeoxycholic ursodeoxycholic acid for prevention of gallstones;

medications used in the field of cardiology: cardiac inotropes including digoxin, enoximone, and milrinone; diuretics including thiazides (bendroflumethiazide, chlortalidone, cyclopenthiazide, indapamide, metolazone, xipamide), loops (bumetanide, furosemide, torasemide), potassium sparing agents (amiloride hydrochloride, triamterene), and aldosterone antagonists (spironolactone, eplerenone); anti-arrhythmic drugs including dronedarone, digoxin, verapamil, amiodarone hydrochoride, disopyramide, flecainide acetate, procainamide, propafenone hydrocholride, and beta-blockers (propranolol hydrochloride, acebutolol, atenolol, bisoprolol fumarate, carvedilol, celiprolol hydrochloride, esmolol hydrochloride, labetolol hydrochloride, metoprolol tartrate, nadolol, nebivolol, oxprenolol hydrochloride, pindolol, sotalol hydrochloride, timolol maleate), ivabradine, ranolazine;

other medications including anti-hypertensive drugs including hydralazine hydrochloride, prazosin, doxazosin, indoramin, terazosin, sildenafil, methyldopa, clonidine hydrochloride, and moxonidine; drugs used in heart failure or hypertension including captopril, cilazapril, enalapril maleate, fosinopril sodium, imidapril hydrochloride, lisinopril, moexipril hydrochloride, perindopril erbumine, perindopril arginine, quinapril, rampiril, trandolapril, candesartan cilexetil, erposartan, irbesartan, losartan potassium, olmesartan medoxomil, telmisartan, valsartan, and aliskiren, vasodilators include glyceryl trinitrate, isosorbide dinitrate, isosorbide mononitrate, amlodipine, diltiazem hydrochloride, felodipine, isradipine, lacidipine, lercanidipine hydrochloride, nicardipine hydrochloride, nifedipine, nimodipine, verapamil hydrochloride, nicorandil, cilostazol, inositol nicotinate, moxisylyte, naftidrofuryl oxalate, and pentoxifylline;

further medications including anticoagulants comprising heparin, dalteparin sodium, enoxaparin sodium, tinzaparin sodium, danaparoid sodium, bivalirudin, lepirudin, fondaparinux sodium, warfarin sodium, acenocoumarol, phenindione, dabigatran etexilate, apixaban, and rivaroxaban; antiplatelet drugs including aspirin, clopidogrel, dipyridamole, prasugrel, and ticagrelor; lipid regulating drugs including atorvastatin, fluvastatin, pravastatin sodium, rosuvastatin, simvastatin, ezetimibe, bezafibrate, ciprofibrate, fenofibrate, gemfibrozil, acipimox, and nicotinic acid;

respiratory medications comprising: drugs affecting the airways including bambuterol hydrochloride, formoterol fumarate, indacaterol, salbutamol, salmeterol, terbutaline sulphate, ephedrine hydrochloride, ipratropium bromide, tiotropium, theophylline, aminophylline, beclomethasone dipropionate, budesonide, ciclesonide, fluticasone propionate, mometasone furoate, sodium cromoglicate, nedocromil sodium, montelukast, and zafirlukast, roflumilast; antihistamines including acrivastine, bilastine, cetirizine hydrochloride, desloratadine, fexofenadine hydrochloride, levocetirizine hydrochloride, loratadine, mizolastine, rupatadine, alimemazine tartrate, chlorphenamine maleate, clemastine, cyproheptadine hydrochloride, hydroxyzine hydrochloride, ketotifen, and promethazine hydrochloride;

drugs having a central nervous system effect comprising: anti-anxiety medication including nitrazepam, flurazepam, loprazolam, lormetazepam, temazepam, zaleplon, zolpidem tartrate, zopiclone, chloral hydrate, clomethiazole, sodium oxybate, diazepam, alprazolam, chlordiazepoxide hydrochloride, lorazepam, and oxazepam; anti-psychotic medication including benperidol, chlorpromazine hydrochloride, flupentixol, haloperidol, levomepromazine, pericyazine, perphenazine, pimozide, prochlorperazine, promazine hydrochloride, sulpiride, trifluoperazine, zuclopenthixol, zuclopenthixol acetate, amisulpride, aripiprazole, clozapine, olanzapine, paliperidone, quetiapine, risperidone, flupentixol decanoate, fluphenazine decanoate, olanzapine embonate, pipotiazine palmitate, and zuclopenthixol decanoate;

further medications including antimanic drugs including asenapine, carbamazepine, valproic acid, lithium carbonate, and lithium citrate; antidepressant drugs including amitriptyline hydrochloride, clomipramine hydrochloride, dosulepin hydrochloride, doxepin, imipramine hydrochloride, lofepramine, nortriptyline, trimipramine, mianserin hydrochloride, trazodone hydrochloride, phenelzine, isocarboxazid, tranylcypromine, moclobemide, citalopram, escitalopram, fluoxetine, fluvoxamine maleate, paroxetine, sertraline, agomelatine, duloxetine, mirtazapine, reboxetine, tryptophan, venlafaxine; antinausea medication includes cinnarizine, cyclizine, promethazine hydrochloride, promethazine teoclate, droperidol, domperidol, metoclopramide hydrochloride, granisetron, ondansetron, palonosetron, aprepitant, fosaprepitant, nabilone, hyoscine hydrobromide, and betahistine dihydrochloride;

analgesic medications including aspirin, paracetamol, nefopam hydrochloride, buprenorphine, codeine phosphate, diamorphine hydrochloride, dihydrocodeine tartrate, dipipanone hydrochloride, fentanyl, hydromorphone hydrochloride, meptazinol, methadone hydrochloride, morphine salts, oxycodone hydrochloride, papaveretum, pentazocine, pethidine hydrochloride, tapentadol, and tramadol hydrochloride; antimaigraine medication includes pizotifen, and clonidine hydrochloride;

antiepileptic medications including carbamazepine, eslicarbazepine acetate, oxcarbazepine, ethosuximide, gabapentin, pregabalin, lacosamide, lamotrigine, levetiracetam, phenobarbital, pimidone, phenytoin, retigabine, rufinamide, tiagabine, topiramate, sodium valproate, vigabactrin, zonisamide, clobazam, and clonazepam; antiparkinsonian medication including apomorphine hydrochloride, bromocriptine, cabergoline, pergolide, pramipexole, ropinirole, rotigotine, levodopa, co-beneldopa, co-careldopa, rasagiline, selegiline hydrochloride, entacapone, tolcapone, amantadine hydrochloride, orphenadrine hydrochloride, procyclidine hydrochloride, and trihexyphenidyl hydrochloride;

drugs used in the treatment of substance dependence including acamprosate calcium, disulfiriam, naltrexone, bupropion hydrochloride, nicotine, varenicline, buprenorphine, methadone hydrochloride, and naltrexone hydrochloride; dementia medication including donepezil, galantamine, memantine hydrochloride, and rivastigmine;

medications used in the management of endocrine conditions including: insulins including intermediate-acting and long-acting preparations; antidiabetic drugs including glibenclamide, gliclazide, glimepiride, glipizide, tolbutamide, metformin, acarbose, exenatide, linagliptin, liraglutide, nateglinide, pioglitazone, repaglinide, saxagliptin, sitagliptin, and vildagliptin, thyroxines including levothyroxine sodium, liothyronine sodium, and armour thyroid; antithyroid drugs include carbimazole and propylthiouracil, steroids including fludrocortisone acetate, betamethasone, deflazacort, dexamethasone, hydrocortisone, methylprednisolone, prednisolone, prednisone, and triamcinolone;

female sex hormones including oestrogens (conjugated equine oestrogens, oestradiol, oestradiol valerate, ethinyloestradiol, oestriol, mestranol and their analogues and derivatives), tibolone, raloxifene hydrochloride, progestogens (progesterone, dydrogesterone, medroxyprogesterone acetate, megestrol acetate, levonorgestrel, dienogest, norethisterone, norethisterone acetate, norgestrel, desogestrel, norgestimate, gestodene, drospirenone, etynodiol diacetate and their analogues and derivatives), and testosterone esters (enantate, propionate, deconoate, undecanoate, phenylpropionate, isocaproate), dehydroepiandrosterone and mesterolone; also selective progestogen-receptor modulators including ulipristal acetate and other members of the same family; also chorionic gonadotrophin, choriogonadotropin alfa, corifollitropin alfa, follitropin alfa and beta, human menopausal gonadotrophins, lutropin alfa, gonadorelin;

other hormones including somatropin, human growth hormone, desmopressin, vasopressin, tolvaptan; hormone antagonists including anastrozole, exemestane, fulvestrant, letrozole, tamoxifen, and toremifene; drugs affecting bone metabolism including calcitonin, parathyroid hormone, teriparatide, bisphosphonates (alendronic acid, disodium etidronate, disodium pamidronate, ibandronic acid, risedronate sodium, sodium condronate, zoledronic acid, denosumab, and strontium ranelate; other endocrine drugs including bromocriptine, cabergoline, quinagolide, cetrorelix, danazol, ganirelix, buserelin, goserelin, histrelin, leuprorelin acetate, nafarelin, and triptorelin;

medications used for treating infections including the following antibiotics: penicillins (benzylpenicillin sodium, phenoxymethylpenicillin, flucoxacillin, temocillin, amoxicillin, ampicillin, co-amoxiclav, co-fluampicil, piperacillin, tazobactam, ticarcillin with clavulanic acid, and pivmecillinam hydrochloride; cephalosporins, carbapenems and other beta-lactams (cefaclor, cefadroxil, cephalexin, cefixime, cefotaxime, cefpodoxime, cefradine, ceftazidime, ceftriaxone, cefuroxime, doripenem, ertapenem, imipenem with cilastatin, meropenem, and aztreonam); tetracycline, demecolcycline hydrochloride, doxycycline, lymecycline, minocycline, oxytetracycline, and tigecycline; aminoglycosides (gentamicin, amikacin, tobramycin), macrolides (azithromycin, clarithromycin, erythromycin, and telithromycin), other antibiotics include clindamycin, chloramphenicol, sodium fusidate, vancomycin, teicoplanin, daptomycin, linezolid, colistimethate sodium, co-trimoxazole, sulfadiazine, trimethoprim, metronidazole, tinidazole, ciprofloxacin, levofloxacin, moxifloxacin, nalidixic acid, norfloxacin, ofloxacin, nitrofurantoin, and methenamine hippurate;

medications for treating other infections including: antifungals comprising fluconazole and itraconazole; antivirals including abacavir, didanosine, emtricitabine, lamivudine, tenofovir disoproxil, zidovudine, atazanavir, darunavir, fosamprenavir, indinavir, lopinavir, ritonavir, nelfinavir, saquinavir, tipranavir, efavirenz, etravirine, nevirapine, enfuvirtide, maraviroc, raltegravir, acyclovir, famciclovir, inosine pranobex, valaciclovir, adefovir dipivoxil, entecavir, telbivudine, boceprevir, and telaprevir; antimalarials including artemether with lumefantrine, chloroquine, mefloquine, primaquine, proguanil hydrochloride, atovaquone, pyrimethamine, sulfadoxine, and quinine; anti TB drugs including capreomycin, cycloserine, ethambutol hydrochloride, isoniazid, pyrazinamide, rifabutin, rifampicin, and streptomycin;

other medications which are used in obstetrics and gynaecology including carbetocin, carboprost, dinoprostone, ergometrine maleate, gemeprost, oxytocin, mifepristone, atosiban, salbutamol, and terbutaline; antifungals including clotrimazole, miconazole, econazole, fenticonazole; drugs used for restoring the vaginal environment including clindamycin, metronidazole, and lactic acid; contraceptives including combined contraception and progestogen-only contraception; using combinations and/or varying amounts of the female sex hormones noted above; varying combinations of the female sex hormones listed above for hormone replacement therapy;

drugs for urinary dysfunction including darifenacin, duloxetine, fesoterodine fumarate, flavoxate hydrochloride, oxybutynin hydrochloride, propantheline bromide, propiverine hydrochloride, solifenacin succinate, tolterodine tartrate, trospium chloride, alfuzosin hydrochloride, doxazosin, indoramin, prazosin, tamsulosin hydrochloride, terazosin, bethanechol chloride, and distigmine bromide; drugs used to aid sexual response including sildenafil, tadalafil, and vardenafil; other medications including interferon alfa, peginterferon alfa, interferon beta, interferon gamma-1b, and immunosuppressants including ciclosporin, tacrolimus, and sirolimus; and, drugs that are used in musculoskeletal & joint disease, including ibuprofen, naproxen, fenoprofen, flurbiprofen, dexketoprofen, ketoprofen, tiaprofenic acid, diclofenac sodium, diclofenac potassium, aceclofenac, etodolac, acemetacin, indomethacin, mefanamic acid, meloxicam, nabumetone, piroxicam, sulindac, tenoxicam, tolfenamic acid, ketorolac, parecoxib, etoricoxib, celecoxib, and other NSAIDs & Cox-2 inhibitors; aspirin; sodium aurothiomalate, penicillamine, chloroquine, hydroxychloroquine sulphate, allopurinol, febuxostat, probenecid, sulfinpyrazone, glucosamine, baclofen, cannabis extract, dantrolene sodium, diazepam, tizanidine, and quinine.

22. A cervical transfer catheter system that transfers a therapeutic substance to a recipient, the cervical transfer catheter system comprising:
 a removable stent containing the therapeutic substance;
 a catheter body having first and second lumens, the catheter body is positionable in an endocervix of the recipient, the second lumen is designed to retain the removable stent after the catheter body has been inserted in a recipient's uterus;
 an inflatable balloon provided at a distal end of the first lumen, wherein when the catheter body is positioned in the endocervix the inflatable balloon is positioned in a uterus of the recipient so as to retain a portion of the catheter body within the recipient's uterus for a minimum period of several hours;
 wherein the balloon comprises first and second arms, which in the inflated condition extend upwards transversely within the recipient's uterus, so that in a side view the inflatable balloon has a V-shape when inflated with an external surface that is convex and that in use contacts a surface of the uterus, and an internal surface opposite the external surface, and the internal surface is generally concave.

* * * * *